US006979298B2

(12) United States Patent
Vodyanoy et al.

(10) Patent No.: US 6,979,298 B2
(45) Date of Patent: Dec. 27, 2005

(54) APPARATUS AND METHOD FOR THE MEASUREMENT OF THE AERODYNAMICS OF OLFACTION IN ANIMALS AND MAN

(75) Inventors: Vitaly J. Vodyanoy, Auburn, AL (US); Edward E. Morrison, Auburn, AL (US)

(73) Assignee: Auburn University, Auburn, AL (US)

( * ) Notice: Subject to any disclaimer, the term of this patent is extended or adjusted under 35 U.S.C. 154(b) by 209 days.

(21) Appl. No.: 10/159,800

(22) Filed: May 31, 2002

(65) Prior Publication Data

US 2003/0130568 A1 Jul. 10, 2003

Related U.S. Application Data

(60) Provisional application No. 60/295,377, filed on Jun. 1, 2001.

(51) Int. Cl.[7] .................................. A61B 5/00
(52) U.S. Cl. ..................... 600/529; 600/586; 119/712
(58) Field of Search ............................. 600/586, 303, 600/532

(56) References Cited

U.S. PATENT DOCUMENTS

| | | | | |
|---|---|---|---|---|
| 4,218,584 | A | * | 8/1980 | Attenburrow ............... 600/552 |
| 5,069,222 | A | | 12/1991 | McDonald, Jr. |
| 6,155,986 | A | | 12/2000 | Brydon et al. |
| 6,338,715 | B1 | * | 1/2002 | Hayes et al. ................ 600/303 |
| 6,561,137 | B2 | * | 5/2003 | Oakman ..................... 119/721 |
| 6,602,209 | B2 | * | 8/2003 | Lambert et al. ............. 600/586 |
| 6,659,960 | B2 | * | 12/2003 | Derksen et al. ............. 600/529 |

OTHER PUBLICATIONS

Gazit, Irit & Terkel, Joseph; Domination of olfactcion over vision in explosives detection by dogs; Applied Animal Behaviour Science 2024; pp. 1-9; Elsevier Science B.V. (2003).

Gazit, Irit & Terkel, Joseph; Explosives detection by sniffer dogs following strenuous physical activity; Applied Animal Behaviour Science 81; pp. 149-161; Elsevier Science B.V. (2003).

Thesen, Aud, Steen, Johan, B., Doving, Kjell B.; Behaviour of Dogs During Olfactory Tracking; J. Exp. Biol. 180; pp. 247-251; The Company of Biologists Limited; Great Britain (1993).

Kester, Douglas A., Settles, Gary S., "Experiments on the External Aerodynamics of Canine Olfaction", 1998 Division of Fluid Dynamics Meeting Program, Nov. 22-24, 1998, Philadelphia, PA.

Settles, G.S., "Nostril Aerodynamics of Scenting Animals", Division of Fluid Dynamics, Nov. 23-25, 1997.

Settles, Gary S., Kester, Douglas A., "A Basic Experiment on the Aerodynamics of Sniffing", 1999 Division of Fluid Dynamics Meeting Program, Nov. 21-23, 1999, New Orleans, LA.

* cited by examiner

Primary Examiner—Robert L. Nasser
(74) Attorney, Agent, or Firm—Gardner Groff, P.C.

(57) ABSTRACT

A system and method for observing, collecting and analyzing olfactory characteristics of a human or animal subject, such as sniffing, breathing and respiratory patterns and sounds. Example applications include the evaluation and training of dogs for explosive and drug detection, clinical diagnostics, scientific research, and identification.

23 Claims, 11 Drawing Sheets

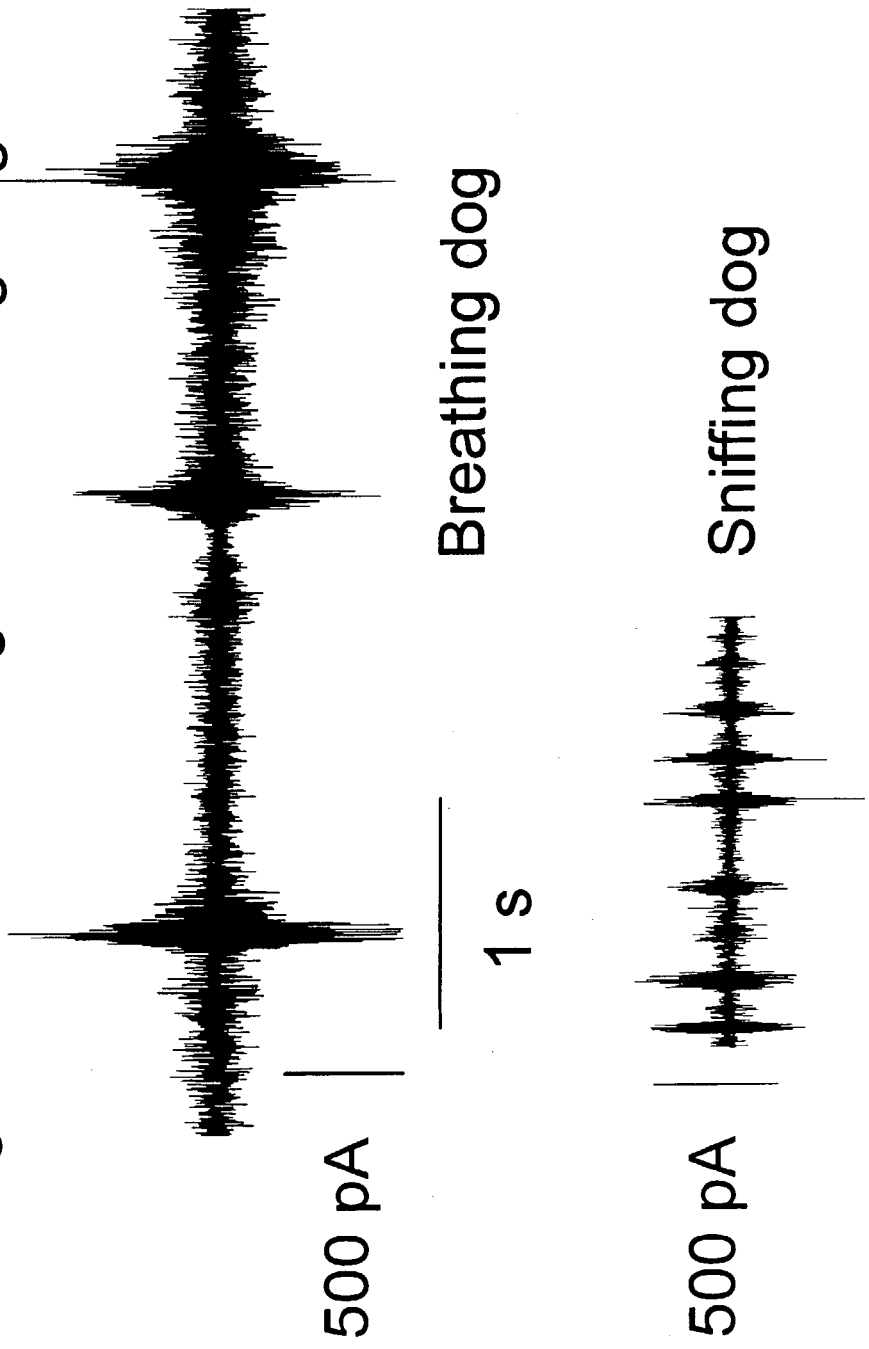

Sound amplitudes recorded from sniffing
dog presented with various odorants
FIG. 8a 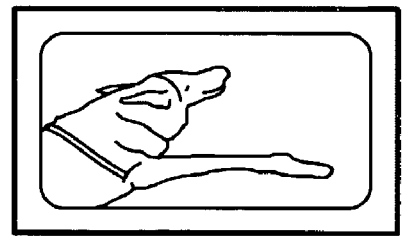 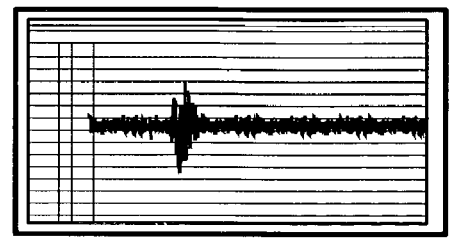
FIG. 8b 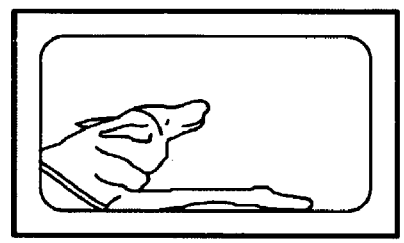 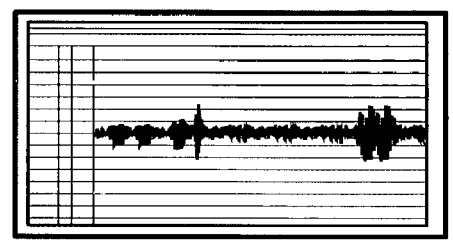
FIG. 8c 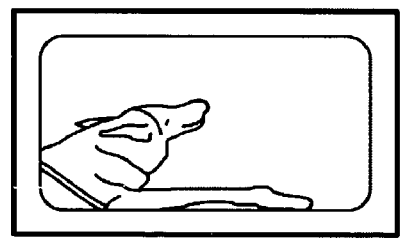 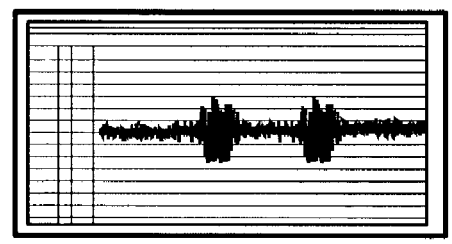
FIG. 8d  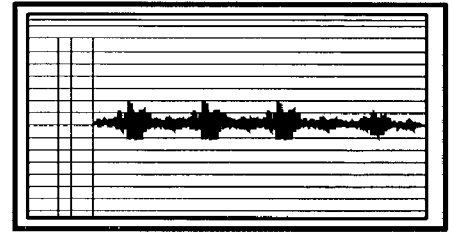
FIG. 8e  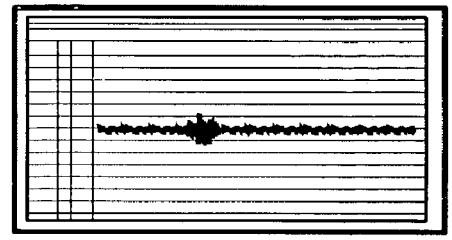

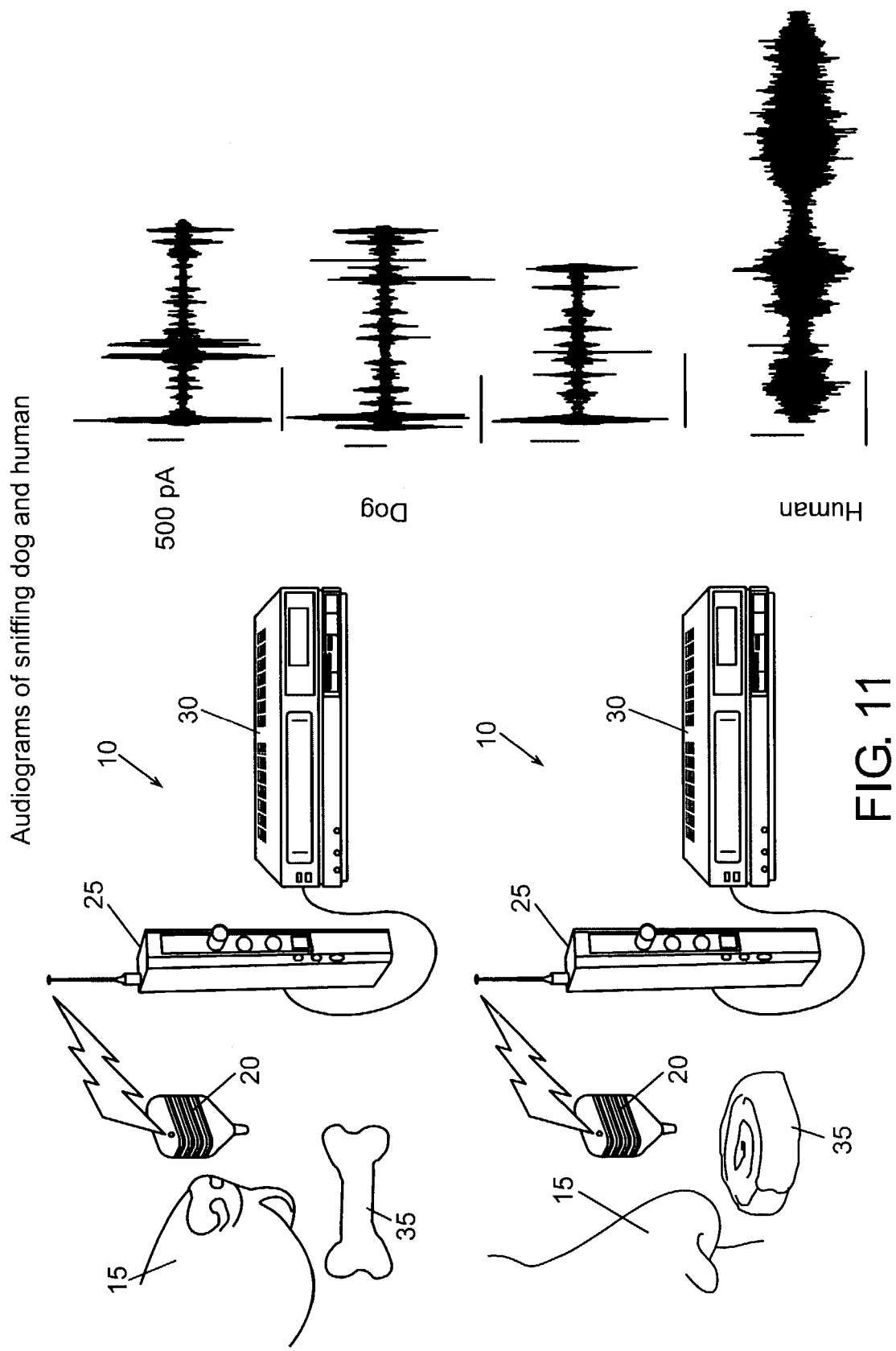

APPARATUS AND METHOD FOR THE MEASUREMENT OF THE AERODYNAMICS OF OLFACTION IN ANIMALS AND MAN

CROSS-REFERENCE TO RELATED APPLICATION

This application claims the benefit of U.S. Provisional Patent Application Serial No. 60/295,377, filed Jun. 1, 2001, which is hereby incorporated herein by reference in its entirety for all purposes.

FIELD OF THE INVENTION

This invention relates generally to the field of olfactory airflow testing devices and methods; and relates more particularly to devices and methods for analysis and measurement of aerodynamics of air flow in and around the nasal cavities of animals and man.

BACKGROUND OF THE INVENTION

The study of how animals and man collect vapor and move it to the operational part of their olfactory systems (the olfactory epithelium) is a developing area of inquiry. A project conducted in the Auburn Institute of Biological Detection Lab involved training dogs to wear a thermocouple placed at the entrance to one nostril so that the changes in the velocity of the inspired and expired air could be used to measure individual sniffs. The dogs were then tested with different types of odors under different conditions to develop information about airflow patterns in the nose while sniffing. This research indicated that a baseline period of respiration followed by a bout of high rate sniffing, which ceases when the odor is removed.

Flow visualization has been used to observe canine olfactory airflows. Two general types of such flows have been observed: high-frequency ("short") sniffing during close inspection of an object and low-frequency ("long") sniffing of more distant objects. In both cases the inspiratory airflow pattern is essentially an inviscid sink flow. However, a comparison of the two types of olfaction shows that the dog has some directional control over the twin turbulent jets generated from its nostrils during expiration. During close inspection of a scent source from directly above, the canine nostrils direct the expired air rearward, so that it does not impinge upon the object. However, when "scanning" the vicinity of a scent source on the ground, the motion of the dog's nose can aim its expiratory jets directly at the source. If particulates are present, they are then readily entrained and can be subsequently inspired. No significant distinction was observed between pet animals and a trained explosive detection dog regarding this behavior.

Without appropriate aerodynamic sampling, the extraordinary sensitivity of canine olfaction typically is not achieved. Current research seeks to understand the aerodynamics of the olfaction process through a series of flow visualization experiments as well as modeling efforts. Flow visualization is used to understand the aerodynamics of the canine nostril. Light-scattering techniques using Schlieren optics have been used to monitor the movement of airborne particles during olfaction.

Oro-nasal respiration of a subject can be monitored by measuring nasal pressure using an electrical pressure transducer. For example, a pair of nasal prongs can be provided, suitable for insertion into the lower portion of the subject's nares, and joining together via a small plenum chamber to form a single tube conveying the nasal pressure towards an electrical pressure transducer. Another prong is held in proximity with the subject's mouth. A baffle element extends downwards from a location above the open end of the prong to redirect a portion of oral airflow. The oral tube extends towards the electrical pressure transducers and conjoins with the nasal tube at a junction to form a common tube connected to the pressure transducer. The relative lengths and/or diameters of the nasal tube and the oral tube are arranged so that the respective pneumatic impedances are different, so that the contributions of respiratory airflow from each of said tubes are substantially equal.

Respiration may also be monitored by thermocouples. A sensor set is used with a monitor to monitor the respiration of a subject. In one arrangement, the sensor set includes a pair of spaced-apart parallel nasal thermocouple junctions, and an oral thermocouple junction aligned with one of the nasal thermocouple junctions. These junctions are supported by a support structure and are coupled to the monitor by a lead set and connector set. The sensor set is easily positioned on the subject's upper lip by looping the lead wires over the subject's ears and securing them underneath the subject's chin. The subject's respiration produces a temperature differential between the thermocouple junctions and a cold or reference junction, producing an output that is sensed by a monitor to indicate respiration. An alternative configuration employs thermistors as the sensor elements.

Known monitoring systems, however, have not proven fully adequate in the measurement and study of olfactory airflow. Thus, it can be seen that needs exist for improved testing devices and methods for analysis and measurement of airflow in and around the nasal cavities of animals and man. It is to the provision of improved testing devices and methods meeting these and other needs that the present invention is primarily directed.

SUMMARY OF THE INVENTION

The present invention provides an apparatus and method for monitoring the aerodynamics of the nose and respiration of an animal and/or human subject. For example, an embodiment of the invention is an apparatus to detect airflow patterns in the nose, which may be used to monitor both "sniffing" patterns and respiration in animals and/or man. Another embodiment of the invention is a method for monitoring the amplitude of the sounds created by "sniffing" or breathing.

In another embodiment, the present invention is a method for attaching a miniature transmitting microphone to the nose of an animal and/or man to detect sounds resulting from the subject's sniffing patterns. Another embodiment of the invention is a method for the transmission of and measurement of the amplitude of the sound detected in the nose of a subject during sniffing.

In one aspect, the invention is a system for monitoring olefactory characteristics of a subject, the system comprising a transmitting microphone for attachment at or near a nasal region of the subject, a receiver for receiving a signal from the microphone, and a recorder for recording data corresponding to the signal received by the receiver.

In another aspect, the invention is a method for monitoring olefactory characteristics of a subject, said method comprising the steps of attaching a microphone at or adjacent a nasal region of the subject, presenting at least one olefactory stimulus to the subject, receiving signals from the microphone corresponding to the olefactory characteristics of the subject, and recording data corresponding to the olefactory characteristics of the subject as a function of the presentation of the at least one olefactory stimulus.

In yet another aspect, the invention is a method of evaluating at least one sniffing characteristic of an animal trained to identify a target material. The method preferably includes attaching a microphone at or adjacent a nasal region of the animal to detect the at least one sniffing characteristic of the animal; and monitoring the at least one sniffing characteristic detected by the microphone.

In another aspect, the invention is a method of clinical diagnosis. The method preferably includes attaching a microphone to a subject to monitor at least one characteristic of the subject; analyzing a chemical content of exhaled breath of a subject; and determining a condition of the subject based on said monitored characteristic and said chemical content.

In another aspect, the invention is a method of monitoring the breathing of a subject. The method preferably includes observing the breathing pattern of the subject; comparing the breathing pattern of the subject to a known breathing pattern; and providing feedback to the subject based on said comparison.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are explanatory of example embodiments of the invention, and are not restrictive of the invention, as claimed.

BRIEF DESCRIPTION OF THE DRAWINGS

FIG. 7 shows the comparative audiograms of a sniffing and breathing dog.

FIG. 8 shows sound amplitudes measured and recorded from a sniffing dog presented with various olfactory stimulants.

FIG. 11 shows dog and human subjects connected to a system according to an example embodiment of the present invention, as well as audiograms of sniffing in each subject.

DETAILED DESCRIPTION OF EXAMPLE EMBODIMENTS

Figure 1:
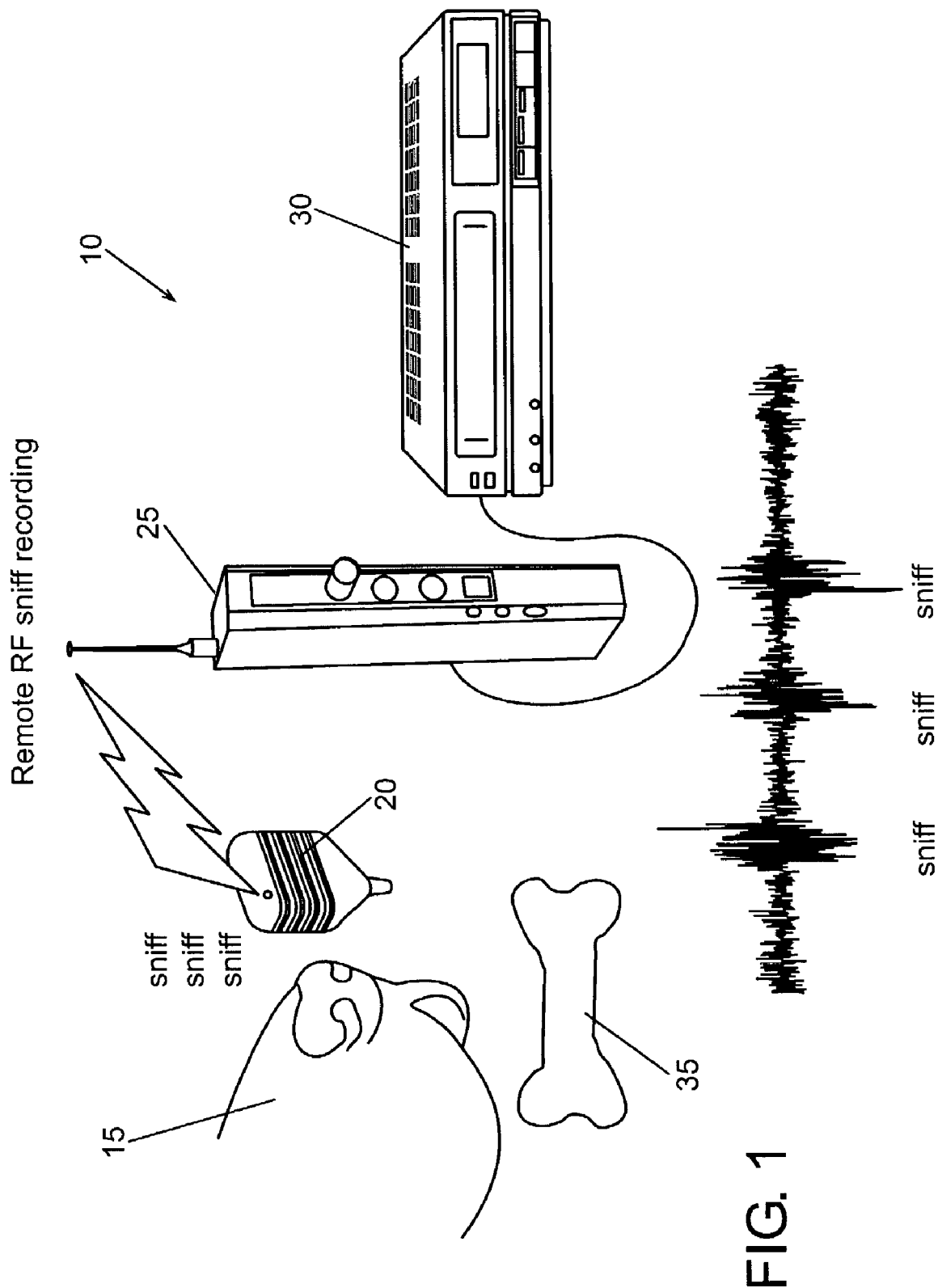
FIG. 1 shows an apparatus and method according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In an example embodiment, the present invention is a system and method for monitoring and/or analyzing olefactory characteristics of an animal or human subject 15, including without limitation characteristics such as sniffing frequency, sniffing amplitude, breathing frequency, breathing amplitude, nasal airflow patterns, and/or olefactory epithelium sounds. The components of a system 10 for monitoring and measuring olefactory characteristics such as sniffing frequency, sniffing amplitude, breathing frequency, breathing amplitude, nasal airflow patterns, and/or olefactory epithelium sounds in an animal or human subject 15, according to an example embodiment of the invention, consist of a transmitting microphone 20, a receiver 25 and a recorder 30 for the measurement of the amplitude of the sounds recovered at the site of the nasal passages by the microphone. The system optionally further comprises a display device or printer for observation of collected data, and/or a computer or other processor for assisting in evaluation of collected data.

FIG. 1 illustrates the components of an example system to measure/monitor the aerodynamics of airflow in the nasal cavity constructed in accordance with one embodiment of this invention. The components comprise a small transmitting microphone 20, a receiver 25 for detecting the microphone output signals, and a recorder 30 for recording the sound signals created by the various "sniffing" patterns to selected odorants 35. Specifications for the example components suitable for use in connection with the system of the present invention include, without limitation: Microphone 20: Spectristech™ high-performance wireless microphone (170.905 megaherz); Receiver 25: Radioshack (171.905 megaherz); Recorder 30: Emerson Video-recorder. Of course, those skilled in the art will recognize that various other components and combinations of components may be used in alternate embodiments of the invention. For example, microphone frequencies of from 2–3 Hz to 20 KHz or more may be adapted for use in connection with the system and method of the present invention.

Figure 2:
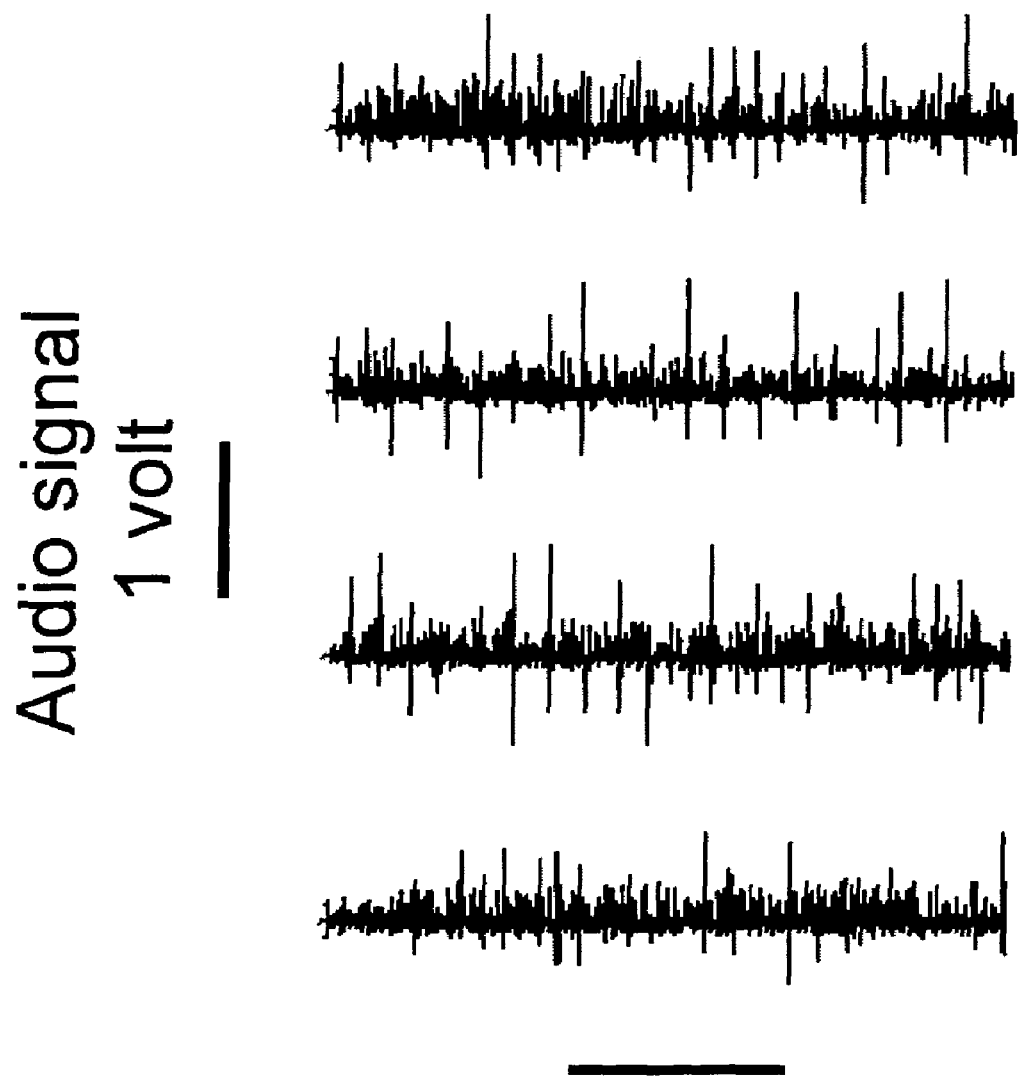
FIG. 2 shows sound amplitudes measured and recorded from a sniffing dog muzzle as a function of time, according to an example embodiment of the present invention.

FIG. 2 depicts sound amplitudes measured and recorded as a function of time, from a sniffing dog muzzle according to an example embodiment of the invention. Individual sniffs are recognizable as sudden bursts in amplitude as the dog responds to various olfactory stimulants.

Figure 3:
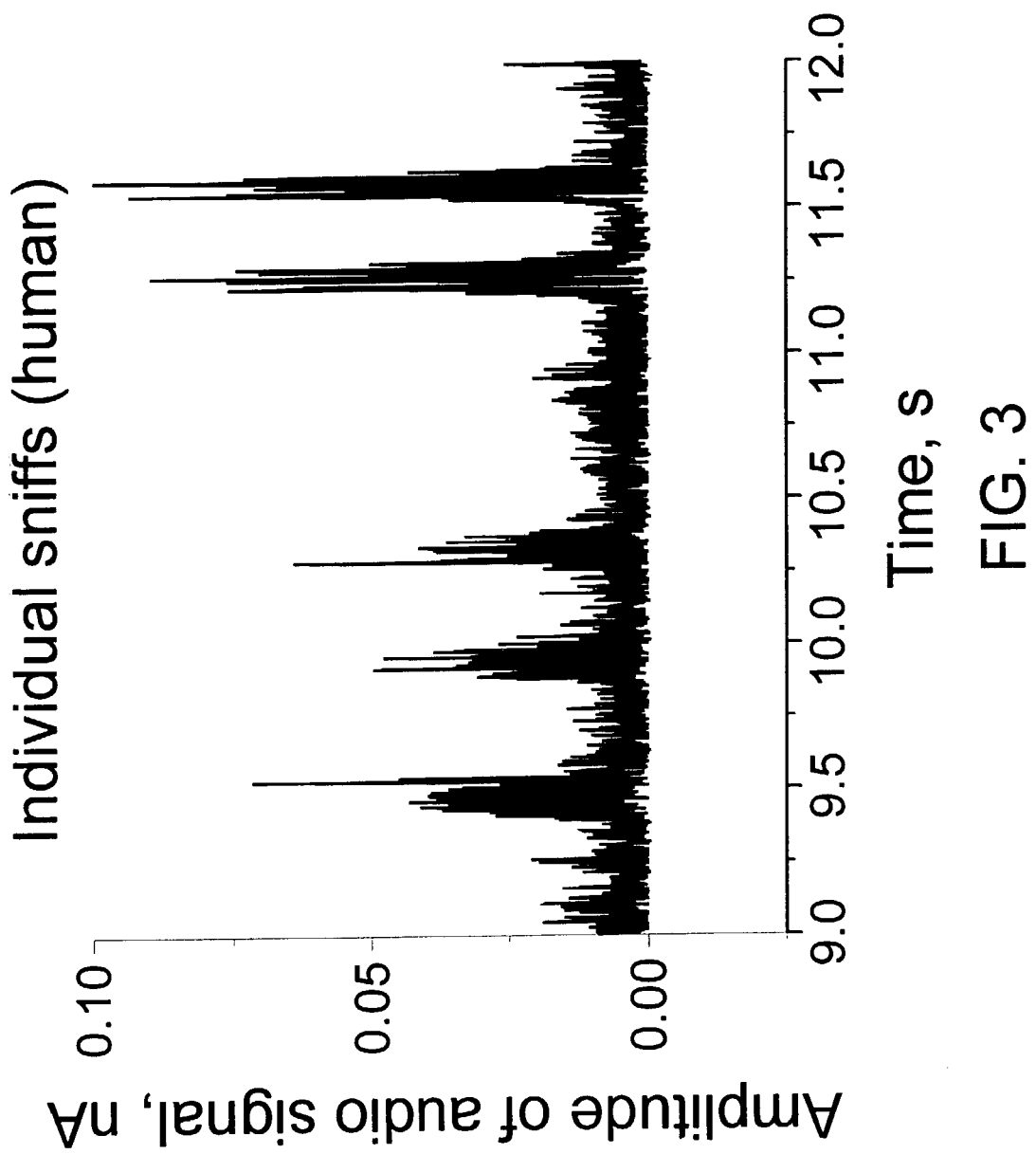
FIG. 3 shows sound amplitudes measured and recorded from a human nose as a function of time.

FIG. 3 depicts sound amplitudes measured and recorded from a human nose as a function of time. Amplitudes are absolute values of the audio current. Again, individual sniffs are recognizable as sudden bursts in amplitude as the person responds to olfactory stimuli.

Figure 4:
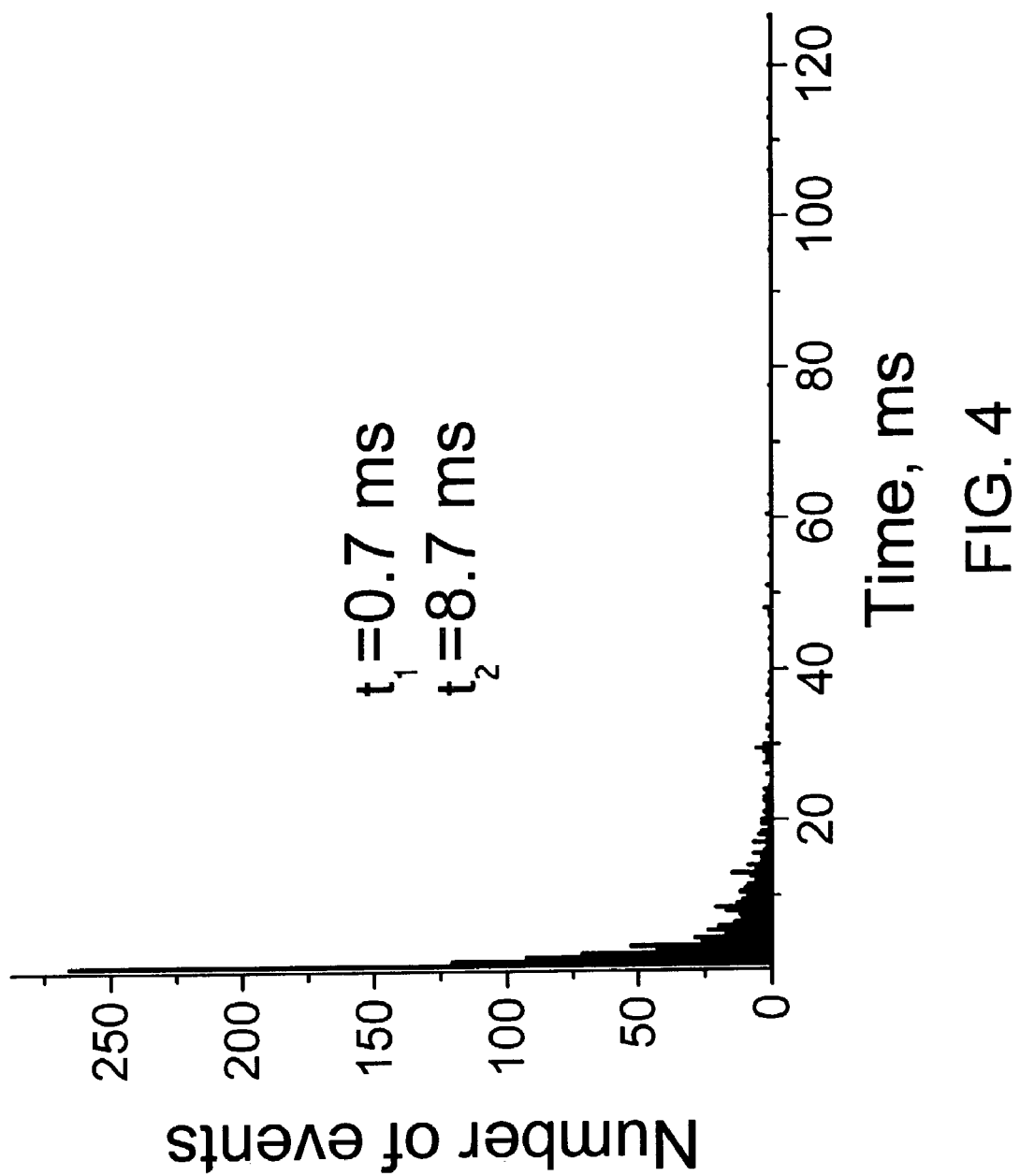
FIG. 4 shows a simple frequency analysis of a human audiogram.
Figure 5:
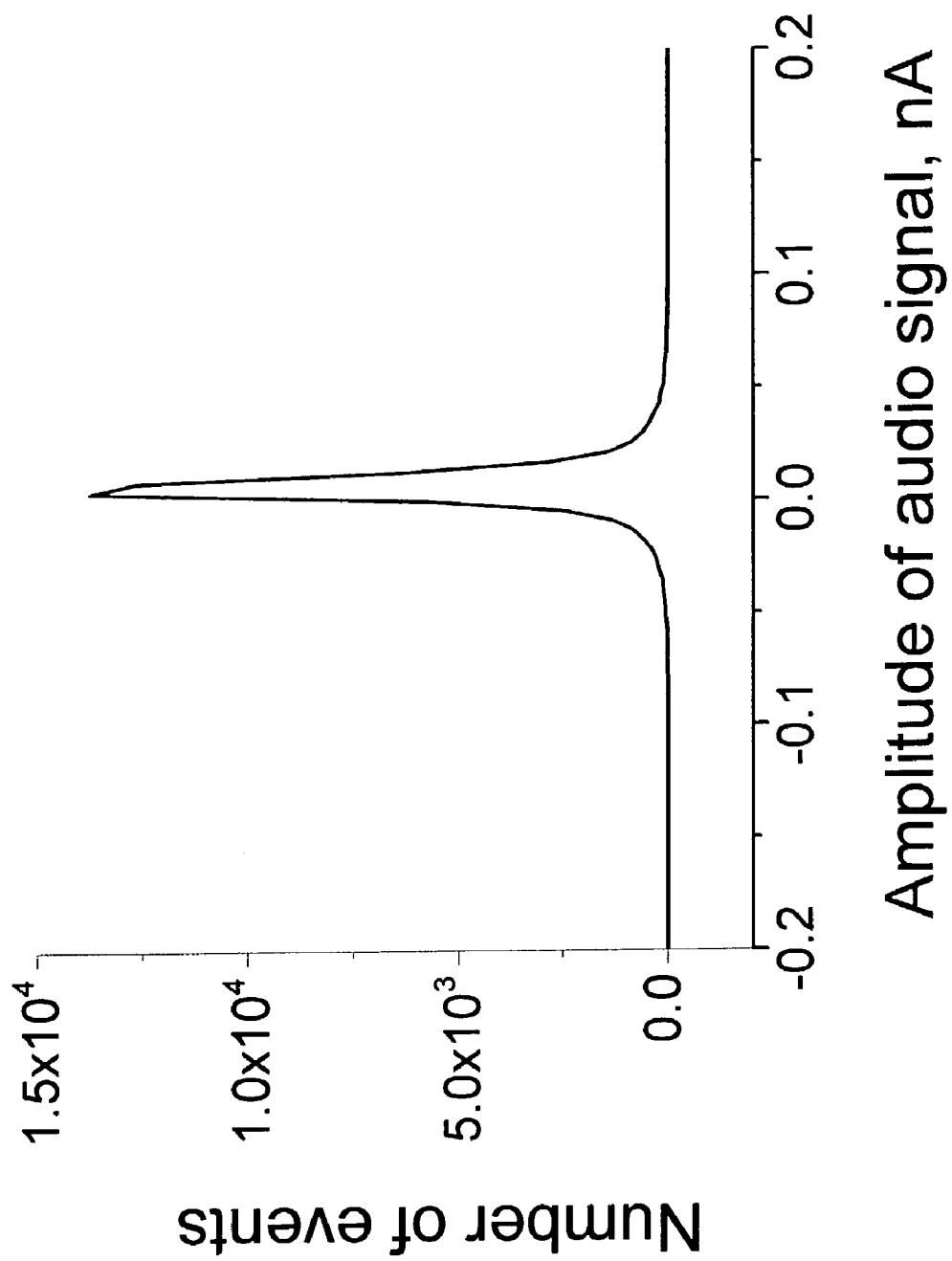
FIG. 5 shows the amplitude distribution of a human audiogram.

FIG. 4 depicts a simple frequency analysis of a human audiogram (time distribution). The frequencies range from low (0.7 milliseconds) to high frequencies (8.7 milliseconds). FIG. 5 depicts the amplitude distribution of a human audiogram.

Figure 6:
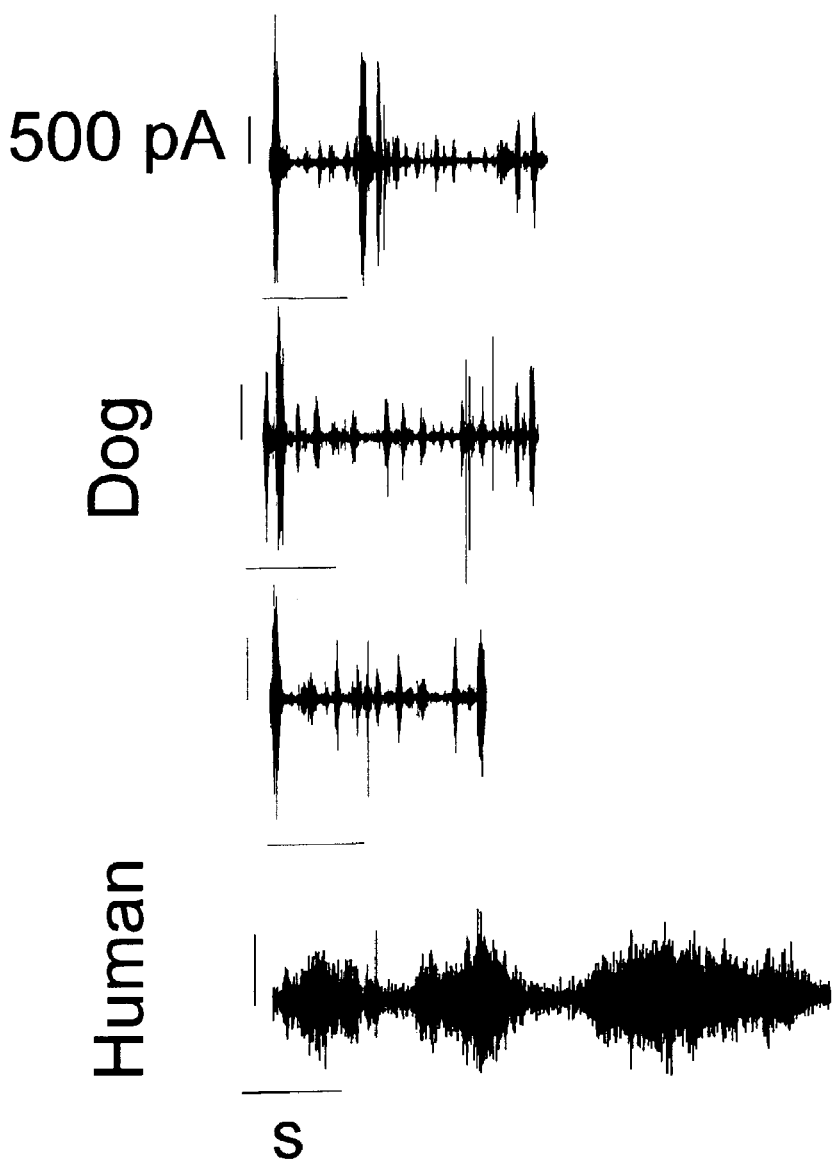
FIG. 6 shows the comparative audiograms of a sniffing dog and a human subject.

FIG. 6 depicts the comparative audiograms of a sniffing dog and a human subject. Note the frequency distribution differences between man and dog. FIG. 7 depicts the comparative audiograms of a sniffing and breathing dog. Note the differences in frequency distribution between the normal breathing cycle versus the sniffing in response to an odorant.

FIG. 8 depicts sound amplitudes measured and recorded from a sniffing dog presented with various olfactory stimulants. Note the differences in frequency distribution and amplitude of recorded sounds as different odorants are detected.

Figure 9:
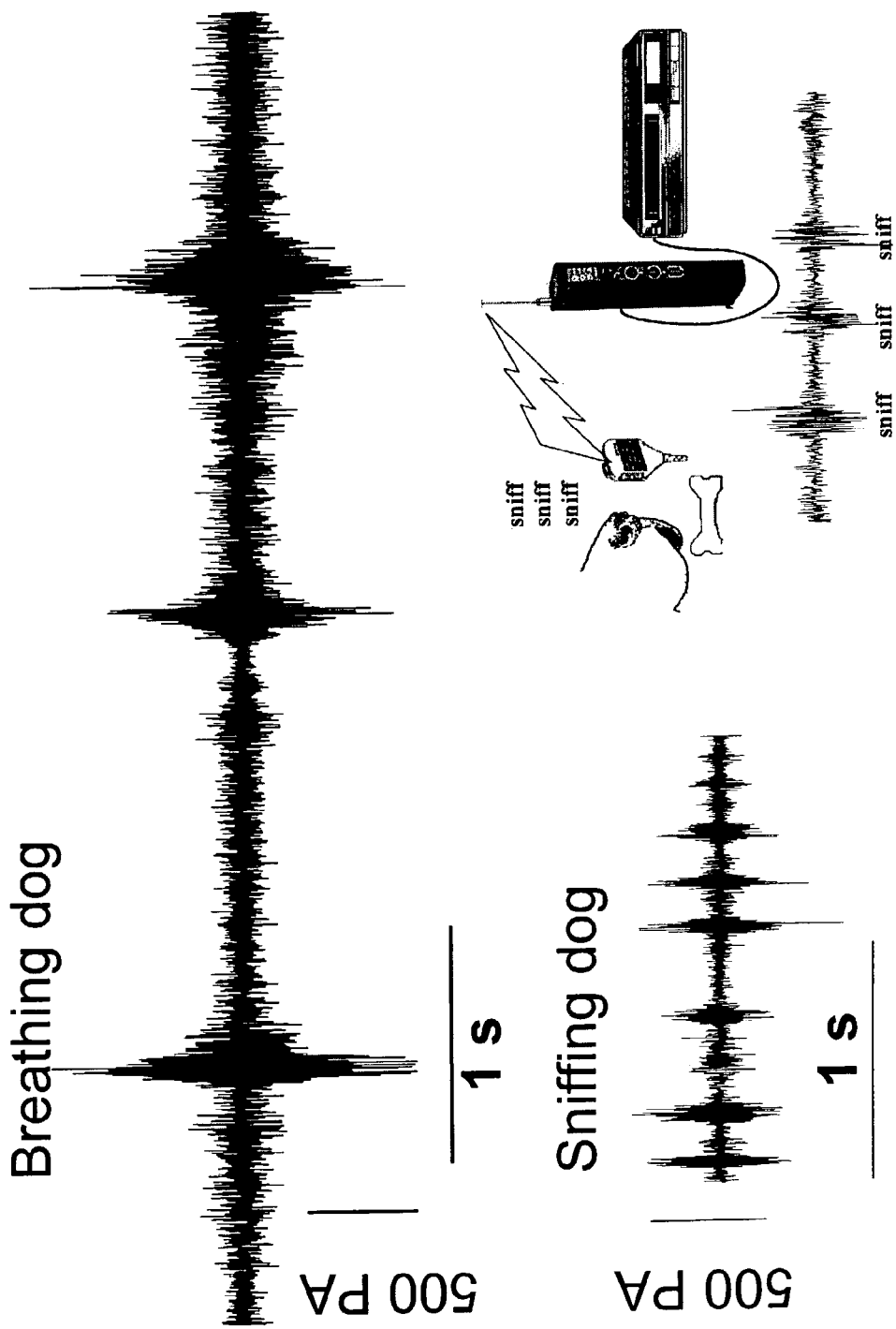
FIG. 9 shows audiograms of breathing and sniffing of a dog subject.
Figure 10A:
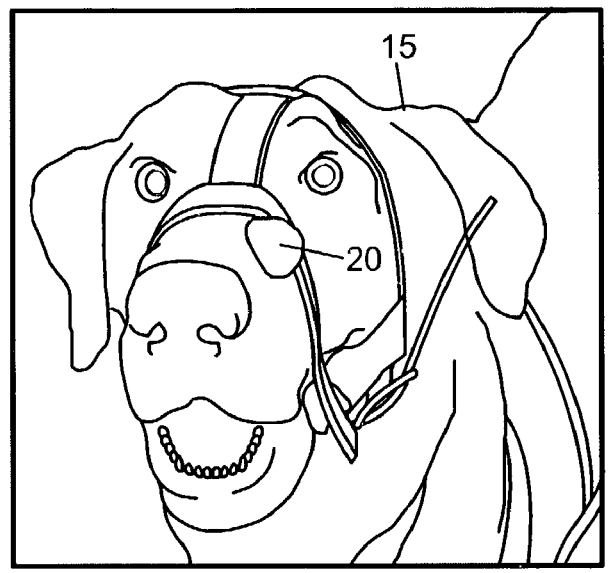
FIG. 10 shows a dog subject connected to a system according to an example embodiment of the present invention.
Figure 10B:
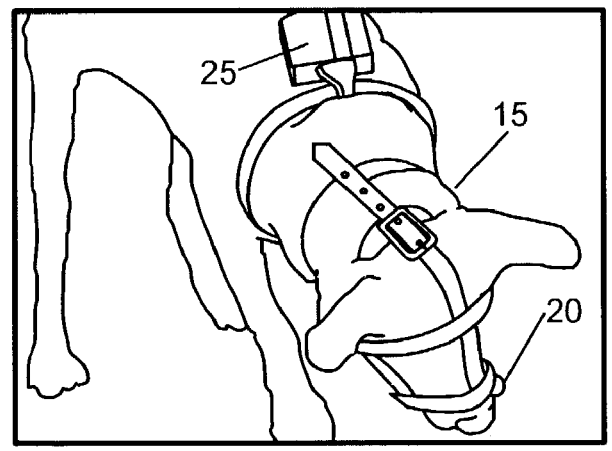
Figure 10C:
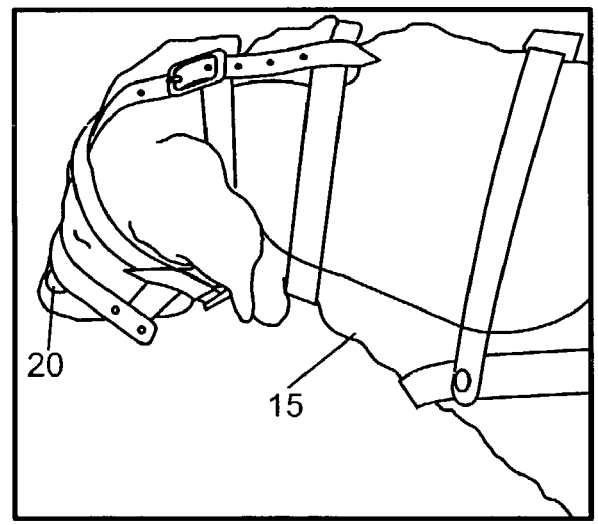

FIG. 9 shows audiograms of breathing and sniffing of a dog subject. FIG. 10 shows a dog subject connected to a system according to an example embodiment of the present invention. FIG. 11 shows dog and human subjects connected to a system according to an example embodiment of the present invention, as well as audiograms of sniffing in each subject.

In example embodiments, one or more microphone(s) 20 is/are mounted to a harness adapted to be secured on or adjacent the nose or head of a human or animal subject. In other forms, the microphone(s) is/are attached to or integral with a dog collar, eyeglasses, a cap, or other garment or item worn by a human or animal subject. The microphone(s) is/are preferably positioned adjacent a nostril of the subject, or on the exterior of the nose in a position generally overlying the olefactory epithelium of the subject. In a typical adult human subject, a microphone position along the side of the nose about ½" above the nostril will overlie the olefactory epithelium.

The microphone(s) 20 of the system pick up sounds and/or vibrations from the nostril intake and/or outflow, and transmit a corresponding signal to the receiver 25, which in turn communicates a corresponding signal that is recorded by the recorder 30 for observation and/or analysis. In alternate embodiments, the signal is transmitted to a computer for recording in memory, for analysis, and/or for display on the computer's monitor. In still further alternate embodiments, the microphone communicates a signal directly to a recorder or computer, for example through a wired connection or through the use of a portable recorder or computer carried by the subject.

The system and method of the present invention may find particular application in various fields. For example, in one aspect the present invention is a system and method for training dogs or other animals for the detection of explosives or drugs. Sniffing or other olefactory characteristics of young candidates for training can be compared to those same characteristics of more experienced dogs that have proven to be particularly successful at their trained task. Training efforts (and the related expenses) can then be focused on those candidates with the target characteristics most like those that have proven successful, or those deemed to indicate the most potential for success. In this manner, the effort and expense of training dogs with lower potential for a particular task can be avoided, and/or working dogs can be trained for the tasks for which they show the greatest potential.

The present invention also includes a system and method for relating olefactory characteristics to a particular olefactory stimulus. It has been observed that certain olefactory characteristics differ depending on the stimulus under observation. For example, a dog trained to sniff out a target material such as drugs or explosives will exhibit one sniffing pattern, designated a "searching" pattern when seeking out the target material, and another sniffing pattern, designated a "presentation" pattern when the target material is presented to or located by the dog. The dog may also exhibit a "resting" state and/or a "respiration" state wherein no sniffing occurs. By monitoring the sniffing pattern of the dog, the handler is alerted to the presence of the target material when the dog shifts from the searching pattern or resting state to the presentation pattern.

In another aspect, the present invention is a system and method for screening human candidates for positions requiring particular olefactory characteristics, such as for example, wine or beer tasters, scotch tasters, and/or perfume testers. Olefactory characteristics of particularly successful practitioners can be collected and analyzed using the system and method of the present invention, to determine what characteristics these individuals may have that set them apart from the general population and lead to their success in a given field. The olefactory characteristics of candidates for that field of endeavor can then be collected and compared to those characteristics found to be indicative of a potential for success in the field. Those candidates with the desired characteristics can then be selected for training or further evaluation.

The system and method of the present invention can also be used to collect data for various fields of scientific research. For example, the function of certain regions or cavities of the olefactory epithelium are unknown. Collection and analysis of data regarding olefactory characteristics using the system and method of the present invention may provide researchers with insight into the function of the smell sense and/or the physical characteristics of the olefactory organs and an individual's sniff patterns and how they may relate to the smell sense.

The system and method of the present invention are also suited for clinical applications in human and veterinary medicine. For example, it has been observed that certain respiratory dysfunctions and other conditions, including lung disease, heart disease, respiratory distress syndrome, asthma, emphysema, allergic responses, pulmonary muscle conditions and diabetes can affect a subject's breathing patterns. Using the system and method of the present invention, a clinician observes the subject's breathing patterns and compares them to known indicators of irregular conditions for diagnosis purposes and for the prediction and treatment of disease. Various alternate microphone positions, such as the subject's throat and/or chest may be utilized in addition to or in place of the nasal microphone position in this aspect of the invention.

Clinical diagnostic applications of the present invention optionally also incorporate breath chemistry analysis in combination with observation of the subject's breath pattern. For example, the exhaled breath of a subject is sampled and analyzed to determine the presence and/or content of various chemical constituents. Observation and analysis of this data, in combination with the subject's breath pattern can be used for diagnosis and monitoring the treatment of various diseases or conditions.

Another application of the system and method of the present invention is in forensics or the identification of a subject. For example, it has been observed that different animal and human subjects have different breath patterns and other olfactory characteristics. These patterns and characteristics can be observed and used to pinpoint the identity of a subject, much in the manner of fingerprint or voice analysis identification.

The present invention also includes a system and method of monitoring and/or analyzing the breathing of a human subject, for example an athlete, to assist in training. It has been observed that particular breathing patterns and timing increase an athlete's performance potential. By monitoring the breathing patterns of an athlete, the athlete can be instructed regarding changes to his or her breathing patterns that might improve performance.

The present invention also includes a system and method for monitoring the breathing of infants to prevent sudden infant death syndrome (SIDS). The infant's breathing patterns can be monitored by mounting a microphone on or near the infant (for example on the infant's crib), and sounding an alarm if a normal breathing pattern is interrupted or if a breathing pattern indicating a potential SIDS occurrence is observed. This aspect of the invention can be extended beyond infant monitoring, for example to monitor the breathing of adults with sleep apnea or other conditions, and/or to monitoring the breathing of astronauts, divers or others to whom breathing air is supplied. The breathing of airline pilots, railroad engineers, drivers, and/or others can also be monitored to sound an alarm upon observing a breathing pattern indicating the subject may be falling asleep.

While the invention has been described with reference to preferred and example embodiments, it will be understood by those skilled in the art that a number of modifications, additions and deletions are within the scope of the invention, as defined by the following claims.

What is claimed is:

1. A system for monitoring olfactory characteristics of a subject, the system comprising a transmitting microphone for attachment in a position generally overlying the olfactory epithelium of the subject, a receiver for receiving a signal indicative of an internal olfactory characteristic from the microphone, and a recorder for recording data corresponding to sounds from the olfactory epithelium as a function of the presentation of at least one stimulus presented to the subject.

2. The system of claim 1, further comprising a harness for attaching the microphone over the olfactory epithelium of the subject.

3. The system of claim 1, further comprising a display for displaying data corresponding to olfactory characteristics of the subject.

4. A method for monitoring olfactory characteristics of a subject, said method comprising the steps of attaching a microphone at or adjacent a nasal region of the subject, presenting at least one olfactory stimulus to the subject, receiving signals from the microphone corresponding to the olfactory characteristics of the subject, and recording data corresponding to the olfactory characteristics of the subject as a function of the presentation of the at least one olfactory stimulus.

5. The method of claim 4, further comprising monitoring states of sniffing by a dog subject, including a first state of searching for a target olfactory stimulus and a second state wherein the dog subject is presented with the target olfactory stimuli.

6. The method of claim 4, further comprising monitoring long-range detection of olfactory stimuli by a dog subject wherein sniff patterns of the subject change to alert a handler of the dog subject of the presence of a specific materials.

7. The method of claim 4, further comprising the step of monitoring breathing and the respiratory extent and rate of the subject.

8. The method of claim 4, further comprising the step of monitoring a respiratory dysfunction in the subject.

9. The method of claim 8, further comprising conducting a chemical analysis of exhaled breath of the subject.

10. The method of claim 4, wherein the microphone is attached in a position generally overlying the olfactory epithelium of the subject.

11. A system for monitoring olfactory characteristics of an animal, the system comprising:
a microphone mounted to a harness adapted to be worn by the animal; and
a computer for receiving signals from the microphone and outputting information related to an olfactory characteristic of the animal, wherein the information related to an olfactory characteristic of the animal includes a sniffing frequency of the animal, and wherein the computer compares the sniffing frequency of the animal with a target sniffing frequency.

12. The system of claim 11, wherein the system outputs an alert to a handler of the animal based on the comparison of the sniffing frequency of the animal with the target sniffing frequency.

13. The system of claim 11, wherein the harness holds the microphone over the olfactory epithelium of the animal.

14. A system for monitoring olfactory characteristics of an animal, the system comprising:
a microphone comprising a wireless transmitter;
a harness for mounting the microphone to the animal;
a receiver for receiving a signal from the wireless transmitter of the microphone;
means for recording data related to the signal;
means for processing said data; and
output means for generating an output from said means for processing, wherein said output means comprises an alarm for alerting a handler of the animal.

15. The system of claim 14, wherein the harness holds the microphone over the olfactory epithelium of the animal.

16. A system for monitoring olfactory characteristics of an animal, the system comprising:
a microphone comprising a wireless transmitter;
a harness for mounting the microphone to the animal;
a receiver for receiving a signal from the wireless transmitter of the microphone;
means for recording data related to the signal;
means for processing said data; and
output means for generating an output from said means for processing;
wherein said means for processing compares a sniffing characteristic of the animal to a target sniffing characteristic.

17. The system of claim 16, wherein the harness holds the microphone over the olfactory epithelium of the animal.

18. A method for monitoring olfactory characteristics of an animal, said method comprising:
collecting input data related to the animal's olfaction using a microphone;
processing the collected data using a computer; and
outputting a signal from the computer related to an olfactory characteristic of the animal, wherein the step of outputting a signal comprises triggering an alarm for alerting a handler of the animal.

19. The method of claim 18 wherein the microphone is attached in a position generally overlying the olfactory epithelium of the animal.

20. A system for monitoring olfactory characteristics of an animal, the system comprising:
   a microphone mounted to a harness adapted to position the microphone generally over the olfactory epithelium of the animal;
   a computer for receiving signals indicative of characteristics of the olfactory epithelium of the animal from the microphone and outputting information related to the olfactory characteristic of the animal, wherein the information related to an olfactory characteristic of the animal includes a sniffing frequency of the animal and, wherein the computer compares the sniffing frequency of the animal with a target sniffing frequency.

21. A system for monitoring olfactory characteristics of an animal, the system comprising:
   a microphone comprising a wireless transmitter;
   a harness adapted holding the microphone in a position generally over the olfactory epithelium of the animal;
   a receiver for receiving a signal indicative of an internal olfactory characteristic from the wireless transmitter of the microphone;
   means for recording data related to the signal;
   means for processing said data; and
   output means for generating an output from said means for processing, wherein said output means comprises an alarm for alerting a handler of the animal.

22. A system for monitoring olfactory characteristics of an animal, the system comprising:
   a microphone comprising a wireless transmitter;
   a harness adapted holding the microphone in a position generally over the olfactory epithelium of the animal;
   a receiver for receiving a signal indicative of an internal olfactory characteristic from the wireless transmitter of the microphone;
   means for recording data related to the signal;
   means for processing said data; and
   output means for generating an output from said means for processing, wherein said means for processing compares a sniffing characteristic of the animal to a target sniffing characteristic.

23. A method for monitoring olfactory characteristics of an animal, said method comprising:
   collecting input data related to olfactory epithelium sounds of the animal using a microphone;
   processing the collected data using a computer;
   outputting a signal from the computer related to an olfactory characteristic of the animal, wherein the step of outputting a signal comprises triggering an alarm for alerting a handler of the animal.

* * * * *